(12) United States Patent
Wynne et al.

(10) Patent No.: US 7,125,708 B2
(45) Date of Patent: Oct. 24, 2006

(54) COMPOSITION COMPRISING A LACTOBACILLUS PENTOSUS STRAIN AND USES THEREOF

(75) Inventors: Anthony G. Wynne, Reading (GB); Glenn R. Gibson, Reading (GB); Jonathan Brostoff, London (GB)

(73) Assignee: University of Reading, School of Food Biosciences, Reading (GB)

( * ) Notice: Subject to any disclaimer, the term of this patent is extended or adjusted under 35 U.S.C. 154(b) by 0 days.

(21) Appl. No.: 10/491,381

(22) PCT Filed: Oct. 11, 2002

(86) PCT No.: PCT/EP02/11428

§ 371 (c)(1),
(2), (4) Date: Sep. 3, 2004

(87) PCT Pub. No.: WO03/033681

PCT Pub. Date: Apr. 24, 2003

(65) Prior Publication Data

US 2005/0031601 A1    Feb. 10, 2005

(30) Foreign Application Priority Data

Oct. 12, 2001   (GB) ................................ 0124580.2

(51) Int. Cl.
*C12N 1/20*   (2006.01)
(52) U.S. Cl. .................... 435/252.9; 424/93.45
(58) Field of Classification Search ............ 424/93.45; 435/252.9
See application file for complete search history.

(56) References Cited

U.S. PATENT DOCUMENTS

| 4,839,281 A | 6/1989 | Gorbach et al. ............ 435/34 |
| 5,474,932 A | 12/1995 | Bengmark et al. ....... 435/252.9 |
| 6,214,336 B1 | 4/2001 | Bukowska et al. ...... 424/93.45 |

FOREIGN PATENT DOCUMENTS

| EP | 0 577 904 | 5/1997 |
| EP | 1195095 A2 * | 4/2002 |
| FR | 4430 M * | 9/1966 |
| GB | 1190386 | 5/1967 |
| WO | WO 98/35014 | 8/1998 |
| WO | WO 99 17788 A | 4/1999 |
| WO | WO 00/10582 | 3/2000 |
| WO | WO 00/41707 | 7/2000 |
| WO | WO 00/53202 | 9/2000 |
| WO | WO 00/59308 | 10/2000 |
| WO | WO01/30365 | 5/2001 |
| WO | WO 01/37865 | 5/2001 |

OTHER PUBLICATIONS

Okkers, DJ et al. Characterization of pentocin TV35b, a bacteriocin-like peptide isolated from *Lactobacillus pentosus* with a fungistatic effect on *Candida albicans*. Journal of Applied Microbiology. 1999. 87: 726-734.*

Osawa, R et al. Isolation of tannin-degrading *Lactobacilli* from humans and fermented foods. Applied and Environmental Microbiology. 2000. 66(7):3093-3097.*

Mandar Reet et al: "Antibacterial susceptibility of intestinal *Lactobacilli* of healthy children." Scandinavian Journal of Infectious Diseases, vol. 33, No. 5, 2001, pp. 344-349.

Charteris W P et al: "Antibiotic Susceptibility of Potentially Probiotic *Lactobacillus* Species," Journal of Food Protection, Des Moines; IO, US, vol. 61, No. 12, Dec. 1998, pp. 1636-1643.

Okkers D J et al: "Characterization of pentocin TV35b, a bacteriocin-like peptide isolated from *Lactobacillus pentosus* with a fungistatic effect on *Candida albicans*." Journal of Applied Microbiology, vol. 87, No. 5, Nov. 1999, pp. 726-734.

Lee et al., "Isolation and Identification of lactic acid bacteria for preparation of probiotics", Sanop Misaengmul Hakhoechi, vol. 19, No. 5, pp. 429-432, (1991). [Abstract CAPLUS 1993:537376].

Nobaek et al., "Alteration of Intestinal Microflora Is Associated with Reduction in Abdominal Bloating and Pain in Patients With Irritable Bowel Syndrome", The American Journal of Gasteoenterology, vol. 95, No. 5, pp. 1231-1238, (2000).

Olukoya et al., Characterisation Of The Bacteriocins Produced By *Lactobacillus pentosus* DK7 Isolated from OGI and *Lactobacillus plantarum* DK9 From FUFU, Chem. Mikrobiol. Technol. Lebensm., vol. 15, No. 3/4, pp. 65-68, (1993).

Sen et al., "Effects Of *Lactobacillus plantarum* 299V On Symptoms And Colonic Fermentation In Irritable Bowel Syndrom (IBS)", Gut, Vol. 48(Suppl. I) pp. 51a-59a, (Mar. 2001).

Tyurin et al., "Genetic Nature of *Lactobacillus* antibiotic resistance", Antibiot. Khimioter, vol. 34, No. 7, pp. 539-545, (1989).

Van Reenen et al., "Evaluation of Numerical Analysis of Random Amplified Polymorphic DNA (RAPD)-PCR as a Method to Differentiate *Lactobacillus plantarum* and *Lactobacillus pentosus*", Current Microbiology, vol. 32, pp. 183-187, (1996).

Wagner et al., "Biotherapeutic Effects of Probiotic Bacteria on Candidiasis in Immunodeficient Mice", Infection and Immunity, vol. 65, No. 10, pp. 4165-4172, (Oct. 1997).

International Search Report.

* cited by examiner

*Primary Examiner*—Leon B Lankford, Jr.
*Assistant Examiner*—Susan E. Fernandez
(74) *Attorney, Agent, or Firm*—Gary M. Lobel

(57) ABSTRACT

A novel probiotic strain termed *Lactobacillus pentosus* NCIMB 41114 is capable of preventing growth of pathogenic microorganisms in the GI tract. In particular, this bacterium inhibits *Candida* overgrowth, and can be employed to prevent and treat associated diseases, including IBS and thrush.

14 Claims, 1 Drawing Sheet

COMPOSITION COMPRISING A *LACTOBACILLUS PENTOSUS* STRAIN AND USES THEREOF

FIELD OF THE INVENTION

The invention relates to a new probiotic strain of *Lactobacillus pentosus*, to edible and pharmaceutical compositions incorporating this bacterium, and to medical applications of the bacterium in promoting good health, in particular in stimulating the immune system, in combating Candidiasis, in aiding digestion in general, and in alleviating the symptoms of Irritable Bowel Syndrome (IBS).

BACKGROUND OF THE INVENTION

The healthy resident gut microflora comprises a host of beneficial bacteria, predominantly members of the genera *Lactobacillus* and *Bifidobacterium*. The balance of microorganisms can be disrupted by infection, by alteration in diet, through antibiotic treatment, and by stress or physiological trauma. When this occurs a number of adverse reactions may be triggered. Digestive patterns may be altered, with occurrence of diarrhea, constipation and other symptoms of gut irritability. The immune system may be compromised, with consequent reduced resistance to infectious diseases. Pathogenic bacteria or fungi make take hold and colonise the digestive system or other parts of the body.

Traditionally, fermented milk products such as yogurts have been regarded as healthy foods capable of soothing the digestive system; this observation is now explained by the presence of lactic bacteria. Microorganisms such as *Lactobacilli* and *Bifidobacteria* which can promote health are termed "probiotics". Research has shown that particular probiotic microorganisms can influence the composition of the gut microflora by competing out pathogenic bacteria and yeast. Probiotics are also alleged to promote healing of the intestinal mucosa, for example in patients with milk allergy, by reducing gut permeability and by enhancing local intestinal immune responses. Use of probiotics has been advocated for prophylaxis and treatment of diarrhea and for enhancing the recovery of commensal flora after antibiotic therapy. Anticarcinogenic activity has also been demonstrated in clinical trials with probiotics.

A number of "live" dairy products on the market are claimed to contain particularly high counts of certain probiotic *Lactobacilli* or *Bifidobacteria* species for promotion of digestion and a healthy immune system. However, the full range of desirable probiotic effects is exhibited by only a selected few strains of bacteria. It must also be borne in mind that the survivability of a strain in the gastrointestinal (GI) tract is crucial for the biological efficacy of that strain in situ. In order for the strain to implant and establish itself in the intestine it should ideally adhere to the mucosal surface of the GI tract and be able to survive the rigours of transit, such as exposure to stomach and bile acids.

The present invention concerns a novel probiotic strain of *Lactobacillus*, termed *Lactobacillus pentosus* LPK, which was deposited 28 Aug. 2001 according to the Budapest Treaty at the NCIMB, Aberdeen, UK and has received the accession number NCIMB 41114. In addition to exhibiting characteristics typical of *Lactobacilli* in general, this strain has a further surprising property: it is capable of suppressing the growth of *Candida* species to a degree never previously achieved through use of a probiotic. Furthermore, tetracycline and related antibiotics have no effect on growth of this strain. This unique combination of properties can be exploited to combat undesirable growth of *Candida* in any region of the body. In particular, since *Candida* is considered to be a causative factor in Irritable Bowel Syndrome (IBS), it is envisaged that this novel strain of *L. pentosus* could be employed in treating or preventing that disorder.

SUMMARY OF THE INVENTION

In one aspect of the invention there is provided a strain of *Lactobacillus pentosus* having the deposit number NCIMB 41114.

In a second aspect of the invention there is a provided a biologically pure culture of a *Lactobacillus* strain having all the identifying characteristics of *Lactobacillus pentosus* strain NCIMB 41114.

In a third aspect of the invention there is provided a nutritional or pharmaceutical composition comprising *Lactobacillus pentosus* strain NCIMB 41114.

In a fourth aspect of the invention there is provided a nutritional or pharmaceutical composition or kit comprising *Lactobacillus pentosus* stain NCIMB 41114 and an antibiotic.

In another aspect of the invention there is provided use of *Lactobacillus pentosus* strain NCIMB 41114 as a medicament.

In yet another aspect of the invention there is provided use of *Lactobacillus pentosus* strain NCIMB 41114 in the manufacture of a medicament or nutritional formulation for the promotion of a healthy gut microflora; and for the prophylaxis or treatment of: bacterial or yeast infections; Candidiasis; diarrhea or other gastrointestinal disturbances; Irritable Bowel Syndrome or symptoms thereof; and a weakened immune system.

In a further aspect of the invention there is provided a process of isolating a probiotic strain of lactic acid bacteria, comprising growing a fecal cell culture in the presence of a bactericidal level of tetracycline, and collecting viable lactic acid bacteria cells from the culture; and a lactic acid bacterial strain obtained by this process.

DETAILED DESCRIPTION OF THE INVENTION

Figure 1:
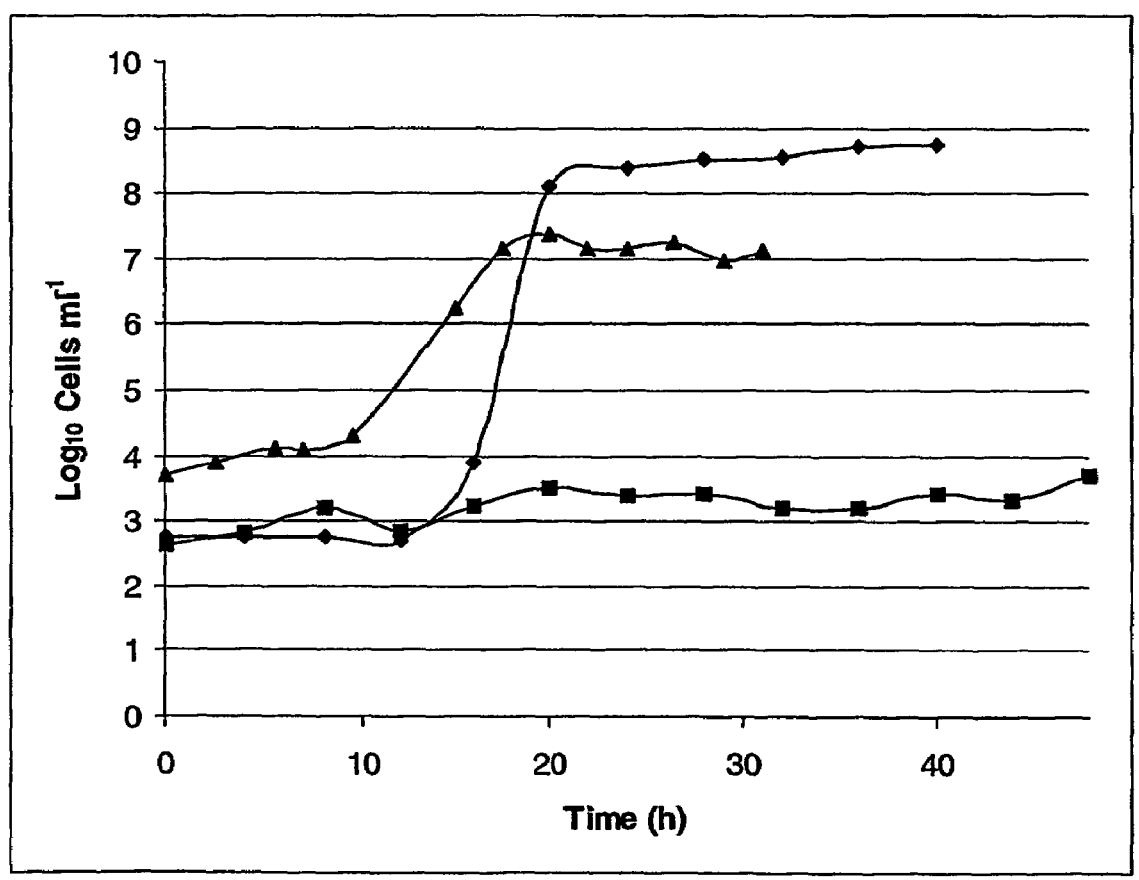
FIG. 1 shows co-culture growth of *Candida albicans* (■) and *L. pentosus* NCIMB 41114 (♦), and pure culture growth of *Candida albicans* (▲) under the same conditions and in identical media.

The novel *L. pentosus* strain which is the subject of the present application was isolated from a fecal culture obtained from a healthy adult individual and cultured in the presence of tetracycline.

Two remarkable and unexpected observations led to the discovery and isolation of this microorganism. Firstly, the *Lactobacillus* strain of the invention, and that bacterial strain alone, survived and flourished in medium containing tetracycline, a broad spectrum antibiotic which killed off all other lactic bacteria in the cultures. Secondly, although *Candida* was present in most fecal cultures from the start, growth of this yeast was stalled in the presence of the *Lactobacillus* of the invention. In contrast, in fecal cultures lacking the novel strain of the invention *Candida* grew to dominate the niche left by bacteria killed off by tetracycline.

The novel bacterium of the invention, and compositions comprising this bacterium are generally beneficial to health, and well tolerated by people of all ages. *L. pentosus* NCIMB 41114 can be employed prophylactically or therapeutically in healthy people to guard against minor ailments such as upset stomach, gastritis, gastric ulcers, mild diarrhea (including antibiotic-associated diarrhea), irregular digestive patterns, heartburn, and other digestive complaints. The effects of promoting healthy gut microflora, immune stimulation, cancer prevention, stimulation of bone growth and cholesterol reduction can also be enjoyed by the general population. The novel bacterium of the invention may also be particularly beneficial to hospitalized patients, individuals living in nursing homes, immunocompromised people, patients taking courses of antibiotic treatment, as well as infants, e.g. newborn infants. For example, the bacterium of the invention may also be used for making the microflora of infants more similar to the microflora of breast-fed infants.

The bacterium of the invention can also be employed to target particular disease conditions, in particular as an alternative to, or in conjunction with, pharmaceutical drug treatment. For instance, infant diarrhea (e.g. that caused by *rotavirus*), cholera, dysentery, and infections with *Shigella*, *E. coli* 0157:H7, *Clostridium difficile* and *Salmonella* may be cured or alleviated through consumption of the bacterium of the invention. For people who are immunocompromised for any reason (e.g. following chemotherapy, leukemia, HIV/AIDS etc.), ingestion of *L. pentosus* NCIMB 41114 can be a very useful prophylactic and therapeutic treatment to prevent or suppress infections by pathogenic microorganisms.

Because *L. pentosus* LPK is resistant to tetracycline and related antibiotics the probiotic benefits of consuming or applying this microorganism continue to be available during treatment with antibiotics.

A major benefit of this *Lactobacillus* species over other known *Lactobacilli* is that the strain is capable of combating yeast overgrowth, especially *Candida* infections. *Candida* infections are typically encountered in certain categories of susceptible individuals, including individuals living in nursing homes, immunocompromised patients such as HIV-positive or AIDS patents, patients undergoing radiation therapy, chemotherapy and bone marrow transplantation, hospitalized patients having increased exposure to *Candida*, newborn infants, women on birth control pills, and anyone taking courses of antibiotic treatment.

Candidiasis may be caused by *Candida parapsilosis*, *Candida tropicalis*, or *Torulopsis glabrata*, but is typically caused by *Candida albicans*.

*Candida albicans* can infect the mouth (oral thrush), urinary tract, vagina (vaginal thrush or vaginitis), oesophagus, intestinal tract and the skin (e.g. diaper rash), leading to irritation, inflammation and other symptoms. These infections are commonly cured through the use of courses of antifungal agents. A role for *Candida* overgrowth in IBS has also been postulated. Current treatments for IBS are primarily pharmaceutical preparations directed at alleviating the symptoms, rather than the underlying cause of the disorder. Although certain strains of probiotic bacteria have been reported to have anti-*Candida* activity, the apparent level of activity has not been sufficiently high to merit much interest among gastroenterologists as a potential therapeutic treatment. Because of the striking ability of *L. pentosus* LPK, i.e. strain NCIMB 41114, to suppress *Candida* growth, the present invention is a break-through approach in treating and preventing *Candida* infections.

Thus, in one aspect of the invention administering an effective amount of *Lactobacillus pentosus* strain NCIMB 41114 can be used in a method of preventing or treating any of: bacterial or yeast infections; Candidiasis, in particular urinary tract infections, e.g. urinary infections, thrush; diarrhea or other gastrointestinal disturbances; Irritable Bowel Syndrome or symptoms thereof; and a weakened immune system. The novel bacterium of the invention may also be used in a method of promoting a healthy gut microflora.

In one embodiment of the invention, there is provided method for the treatment or prevention of: a bacterial or yeast infections, e.g. *candida* infections, urinary infections, thrush, Irritable Bowel Syndrome (IBS) or its symptoms, of diarrhea or other gastrointestinal disturbances comprising administering to a subject in need of such treatment an effective amount of a composition comprising live, attenuated or killed *Lactobacillus pentosus* strain NCIMB 41114.

In another aspect of the invention there is provided method for promoting a healthy gut microflora and for stimulating the immune system comprising administering to a subject in need of such treatment an effective amount of a composition comprising live, attenuated or killed *Lactobacillus pentosus* strain NCIMB 41114.

The nutritional or pharmaceutical compositions of the invention comprising *L. pentosus* NCIMB 41114 can be administered enterally, e.g. orally, parenterally, or by physical contact with skin or mucous membranes. The nutritional or pharmaceutical compositions of the invention may be administered directly into the gut, e.g. through a tube or catheter.

The *L. pentosus* strain of the invention can be cultured on a large scale and used therapeutically in lyophilized, freeze-dried or hydrated form. The novel bacterium of the invention may also be administered in conjunction with a pharmaceutically acceptable carrier substance or nutritional matrix.

In the case of a pharmaceutical preparation, the product may be provided in the form of tablets, capsules, implants, suppositories, pessaries, e.g. vaginal pessaries, powder, solutions, gel, liquid bacterial suspensions, and so on. Slow release forms may be particularly desirable. In one embodiment of the invention the novel *L. pentosus* strain is administered as adjunctive therapy to an antibacterial antibiotic (e.g. tetracycline) treatment course, in order to mitigate the risks and side-effects of the antibiotics. For this purpose the antibiotic and bacterium may be formulated together in a single dosage form. Alternatively the bacteria and antibiotic(s) can be provided in kit form, for separate, simultaneous or sequential use. Another option is to co-administer *L. pentosus* NCIMB 41114 and an antifungal agent, such as those conventionally employed to treat Candidiasis, including fluconazole, itraconazole and clotrimazole. These two components work together to combat fungal growth, and can be made available in a single dosage form or as a kit for separate, simultaneous or sequential administration.

When *L. pentosus* NCIMB 41114 is to be administered in nutritional format, it can be added to any food or beverage products, particularly chilled, frozen or long-life dairy products such as milk, milk based powders, yoghurt, kefir, ice-cream, milk-shakes, cheese, cream, curd, fermented milks, and milk based fermented products, but also soy products, fermented cereal based products, food spreads, baked goods, complete nutritional products, tube feeding formulations, and infant formulas. It is also possible to supply the bacteria in edible formats suitable for feeding to animals, such as horses and companion animals.

Often, it is preferred to culture the bacterial strain of the invention on a fermentable substrate such as milk, or starch-containing substrates such as cereal gruel, and then to use the fermented product in a nutritional composition, e.g. a food or beverage.

In nutritional composition, e.g. food or beverage formulations, the product may comprise one or more nutritional components selected from fat, protein, carbohydrate, fiber, minerals and vitamins in addition to *L. pentosus* LPK bacteria. In view of the importance of fiber in regulating digestion it is preferred that fiber of some sort is included in a nutritional or pharmaceutical product of the invention. It is known that probiotic bacteria are stimulated to proliferate when provided with dietary fiber substrates termed "prebiotic" components. This has advantages in promoting colonization of the GI tract and sustaining the vitality of the culture even after consumption of the probiotic has terminated. Therefore, in a preferred embodiment of the invention the probiotic strain of the invention is administered together with a prebiotc substrate, either in a single common dosage form, or as a kit of parts for simultaneous, separate or sequential administration.

Although the novel strain of *L. pentosus* is capable of delivering health benefits in its own right, the possibility also exists to co-administer this bacterium with any other bacteria known to have probiotic properties.

The strain is preferably added to a food or pharmaceutical carrier in an amount of from about $10^5$ cfu/g to about $10^{11}$ cfu/g, preferably about $10^6$ to about $10^{10}$ cfu/g, and most preferably about $10^7$ to about $10^9$ cfu/g of the carrier. It is preferred that the bacterial strain is administered in live form, but prior to consumption the bacteria may be attenuated or killed.

Typically, administration of at least $10^4$ cfu/day of the strain of the invention will be clinically effective. More preferred daily dosages are in the range from $10^6$ to $10^{12}$ cfu/day. Most preferred is $10^7$ to $10^{10}$ cfu/day.

EXAMPLES

Example 1

Isolation of *L. Pentosus* Strain LPK NCIMB 41114

(i) Continuous culture system: Three chemostats were set up in a parallel; each was maintained under nitrogen gas, at 37° C., pH 6.5 and a dilution rate of 0.066 h$^{-1}$. These conditions were set to resemble conditions typically found in the distal region of the human colon. The chemostats were fed with a control growth medium which comprised (gl$^{-1}$ in distilled water): yeast extract 2, peptone water 2, NaCl 0.1, K$_2$HPO$_4$ 0.04, KH$_2$PO$_4$ 0.04, MgSO$_4$.7H$_2$O 0.01, CaCl$_2$.H$_2$O 0.01, NaHCO$_3$ 2, Tween 80 2, hemin 0.05, Vitamin K1 0.01, cysteine.HCl 0.5, bile salts 0.5, glucose 0.4, starch 3, pectin 2 and arabinogalactan 1. The medium was autoclaved at 121° C. for 30 min and, whilst still hot, placed under nitrogen gas. After the medium had cooled, 1 gl$^{-1}$ of filter sterilised tetracycline or 1 gl$^{-1}$ of filter sterilised nystatin was aseptically added to the medium reservoir. Control chemostats with no antimicrobials added were also run.

(ii) Inoculation: Freshly voided fecal samples were obtained from healthy volunteers (n=6) and 10% (w/v) slurries anaerobically prepared using 0.1 mol l$^{-1}$ phosphate buffer pH 7 (26). None of the volunteers had any previous history of gastrointestinal disorder and had avoided antibiotics for at least 3 months prior to the study. The 300 ml chemostat vessels were half filled with medium and 150 ml of slurry added to each vessel. The system was then left for 24 h to equilibrate before the medium pumps were started. The experiment was repeated with 6 different fecal donors in triplicate for each.

(iii) Microbial culture techniques: A sample was taken from each fecal slurry used as inocula and 1 ml samples were also removed from each chemostat when the fermentation system had reached steady state (after 164 h). These were then serially diluted (6-fold) with pre-reduced half strength peptone water. Each dilution was plated, in triplicate, onto pre-reduced (under an anaerobic, 10% $CO_2$, 10% $H_2$, 80% $CO_2$, atmosphere at 37° C.) agars designed to select for predominant groups of gut bacteria: Wilkins Chalgren (Oxoid) for total anaerobes, Rogosa (Oxoid) for *lactobacilli*, Beerens for *bifidobacteria*, KVLB for *bacteroides*, Reinforced *Clostridia* agar (Oxold)+novobocin 8 mg/l and colostin 8 mg/l for *clostridia* and Azide agar (Oxoid) for Gram positive *cocci*. Each dilution was then plated aerobically on to Nutrient Agar (Oxoid) to select for total aerobes, Sabouraud dextrose agar+chloramphenicol and cyclohexamide for yeast and MacConkey agar No. 3 (Oxoid) for coliforms and incubated at 37° C. After 24–48 h of incubation aerobic colonies were counted and after 48–72 h of incubation anaerobic plates were enumerated. Colonies with different morphotypes were also picked from the plates for gram stain, microscopic examination and phenotypic (biochemical) characterisation to confirm culture identities.

Results: Numbers of predominant gut microorganisms in the six inocula used were maintained after steady state conditions in the control chemostats. This confirmed that the growth medium used was efficient at sustaining such populations in the continuous culture experiments. Hence, any differences in profiles resulting from antibiotic exposure were authentically due to these additions rather than any experimental variation. Yeasts were detected in 4 of the 6 volunteers faecal samples tested.

The effect of tetracycline was to markedly reduce populations of all bacteria tested, compared to controls, thereby confirming its broad spectrum of activity. One interesting observation was that the effect of tetracycline allowed yeasts to increase in the fermentation systems in comparison to control chemostat levels. This has clinical implications for the use of tetracycline and associated risks with yeast overgrowth. In fact, in one of the inocula used here, yeasts were not initially detected, but were enriched for during the tetracycline chemostats.

As expected, yeasts were inhibited in the nysatin chemostats. However, certain bacterial genera were also affected. Principally, this involved a reduction in *lactobacilli* which are common probiotic microorganisms seen as important for gastrointestinal health. The clear indication is that nystatin usage is not conducive for the maintenance of indigenous probiotic levels.

During the tetracycline chemostat experiments, one of the runs produced an unexpected result. Yeast were present at the start of the experiment but, contrary to the general trend observed, did not grow further. Instead a Gram positive rod predominated with no other cell types being detected. Genotypic work was therefore carried out to identify this microorganism.

(iv)16S rRNA isolation and amplification: Total DNA was extracted from the *Lactobacillus* using an InstaGene Matrix (Biorad, Hemel Hempstead, Hertfordshire, UK) according to the manufacturer's instructions. The 16S rRNA genes were then amplified by PCR using conserved primers close to the 3' and 5' ends of the gene. The amplified fragment corresponded to positions ~30 to ~1500 of the *Escherichia coli* 16S rRNA gene. In a final volume of 50 μl, the reaction mixture contained amplification primers, premixed deoxynucleoside triphosphates, MgCl$_2$, template, and Taq DNA polymerase, which was added after a precycling stage whereby the reaction mixture was heated to 96° C. for 4 mins. and then held at 0° C. The PCR amplification conditions were 1 min. at 95° C., 1 min. at 55° C., and 1.5 min. at 72° C. for 30 cycles. Following the final cycle, the reaction was extended at 72° C. for 10 mins. and then held at 10° C. Amplification products were visualized by electrophoresis through a 1% (w/v) agarose gel in 1×TAE (40 mM Tris-acetate, 1 m mol I$^{-1}$ EDTA) containing ethidium bromide (0.5 µg ml$^{-1}$). Reaction products which displayed bands corresponding to the correctly sized products (1500 base pairs for primers pA-pH) were purified using a QIAquick PCR purification kit (QlAgen, Crawley, West Sussex, UK) according to the manufacturer's instructions.

(v) rRNA sequencing: For sequencing of PCR products, approximately 1500 nucleotides proximal to the 5' end of the rRNA were targeted using a dRhodamine terminator cycle sequencing kit (PE Applied Biosystems, Inc., Foster City Calif., USA) and a model 377 automatic DNA sequencer (PE Applied Biosystems, Inc., Foster City Calif., USA). Generated sequences were compared with 16S rRNA gene sequences available in the GenBank/EMBL database using the FASTA program and the Ribosomal Database Project (RDP) to generate percentage identity scores with other bacterial species.

Results: Of the 1600 bases in this gene approximately 1500 were sequenced and showed the organism to be a close relative of *Lactobacillus pentosus* and *Lactobacillus plantarum*, which are phylogenetically similar.

*L. pentosus* LPK was subsequently deposited in accordance with the Budapest Treaty on 28 Aug. 2001 at the NCIMB, Aberdeen, UK and received accession number NCIMB 41114.

Example 2

Interactions between the Isolated *Lactobacillus* and *Candida Albicans*

Experiment 1: *Candida albicans* and a *Lactobacillus* isolated from the chemostats, were grown overnight in Sabouraud Dextrose broth (Oxoid) and MRS broth (Oxoid) respectively. Then 1 ml of each was inoculated into a 750 ml batch fermenter containing the following medium constituents (gl$^{-1}$ in distilled water) yeast extract 2, peptone water 2, NaCl 0.1, K$_2$HPO$_4$ 0.04, KH$_2$PO$_4$ 0.04, MgSO$_4$.7H$_2$O 0.01, CaCl$_2$.H$_2$O 0.01, NaHCO$_3$ 2, Tween 80 2, cysteine.HCl 0.5 and glucose 1.0. The medium was autoclaved at 121° C. for 30 min and, whilst still hot, placed under nitrogen gas. The co-culture fermentation was maintained anaerobically at 37° C. and pH 6.5. Regular samples were taken over 48 h and cell numbers enumerated microscopically. Culture identity was confirmed through a combination of phenotypic and biochemical traits. At the end of the fermentation, 1 ml was removed from the fermenter, serially diluted and plated out onto MRS and Sabouraud Dextrose agars and incubated anaerobically for 48 h.

Experiment 2: *Candida albicans* and the isolated *Lactobacillus* were grown overnight in Sabouraud Dextrose and MRS broths respectively. Six MRS agar (2% w/v) plates were poured to an even depth and reduced anaerobically. The isolated *Lactobacillus* culture was then streaked on to each plate. 7 ml of Sabouraud Dextrose agar (0.7% w/v) was maintained at 50° C. and inoculated with 50 µl of the *C. albicans* culture. This was then poured evenly over the plates streaked with the *Lactobacillus* culture. The plates were incubated anaerobically for 48 h at 37° C. and examined for zones of inhibition. Both experiments were repeated 6 times.

(Unless otherwise Stated, all Chemical were Purchased from the Sigma Chemical Co.)

In Experiment 1 this novel strain of *Lactobacillus* grew well and inhibited the growth of *Candida*, restricting it to the inoculation levels (FIG. 1). In experiment 2, there were large zones of inhibition above the *Lactobacillus* colonies where the *Candida* had been unable to grow (data not shown). The resistance of this strain to antimicrobial attack and its powerful antagonism towards *Candida* spp. has relevance for possible maintenance of gut function during therapy for conditions such as IBS.

On the basis of these experiments, it is anticipated that the microorganism may be applied as an adjunct or alternative to conventional therapy for yeast related conditions such as thrush and IBS.

The invention claimed is:

1. A biologically pure culture of a *Lactobacillus* strain as deposited under accession number NCIMB 41114.

2. A biologically pure culture of a *Lactobacillus* strain having all the identifying characteristics of *Lactobacillus* strain NCIMB 41114.

3. A composition comprising live, attenuated or killed *Lactobacillus* strain NCIMB 41114 and a conventional carrier.

4. The composition according to claim 3 which comprises $10^5$ to $10^{11}$ cfu *Lactobacillus* strain NCIMB 41114 per gram of the composition.

5. A composition comprising *Lactobacillus* strain NCIMB 41114 and an antibiotic.

6. The composition according to claim 5 wherein said antibiotic includes tetracycline.

7. The composition according to claim 5 wherein said antibiotic is an antifungal agent.

8. A composition according to claim 3 which in a daily dosage provides from $10^6$ to $10^{12}$ cfu *Lactobacillus* strain NCIMB 41114.

9. A method of controlling a bacterial infection in a patient in need thereof comprising: administering to said patient a composition comprising *Lactobacillus* strain NCIMB 41114.

10. A method of controlling yeast infection in a patient in need thereof comprising: administering to said patient a composition comprising *Lactobacillus* strain NCIMB 41114.

11. The method of claim 10 wherein said yeast infection includes Candidiasis.

12. A method of controlling irritable bowel syndrome in a patient in need thereof comprising: administering to said patient a composition comprising *Lactobacillus* strain NCIMB 41114.

13. A biologically pure culture of the *Lactobacillus* strain of claim 1 obtained by a process comprising growing a fecal cell culture in the presence of a bactericidal level of tetracycline, and collecting viable lactic acid bacteria cells from said culture.

14. A biologically pure culture of the *Lactobacillus* strain of claim 2 obtained by a process comprising growing a fecal cell culture in the presence of a bactericidal level of tetracycline, and collecting viable lactic acid bacteria cells from said culture.

* * * * *